United States Patent [19]

Nishikawa et al.

[11] 4,298,537

[45] Nov. 3, 1981

[54] PROCESS FOR PRODUCING STEROID COMPOUNDS HAVING AN OXO GROUP IN THE SIDE CHAIN

[75] Inventors: Osamu Nishikawa; Kenji Ishimaru, both of Iwakuni; Toru Takeshita, Hino; Hideki Tsuruta, Iwakuni, all of Japan

[73] Assignee: Teijin Limited, Osaka, Japan

[21] Appl. No.: 97,980

[22] Filed: Nov. 28, 1979

[30] Foreign Application Priority Data

Nov. 30, 1978 [JP] Japan ............................. 53-147232

[51] Int. Cl.$^3$ ............................................. C07J 9/00
[52] U.S. Cl. ............................................. 260/397.2
[58] Field of Search ................................... 260/397.2

[56] References Cited

U.S. PATENT DOCUMENTS 4,179,452 12/1979 Ochi et al. ..................... 260/397.2

OTHER PUBLICATIONS

Chem. Rev. 40 (1947), pp. 15-32.
J.A.C.S. 66 (1944), pp. 723-724.
Rec. Trav. Chim. 69 (1950), pp. 759-767.
J.A.C.S. 79 (1957), pp. 1988-1991.
J.C.S. Chem. Comm. vol. 21 (1973), pp. 825-826.
J. Pharmac. Sci. 59 (1970) 5, pp. 719-721.
Gazz. Chim. et al., 97 (1967) 1, pp. 96-101; 102-108.
J.A.C.S., 68 (1946), p. 2078.
Chem. and Industry (1965), p. 426.
J.O.C. 31 (1966), p. 971.

*Primary Examiner*—Elbert L. Roberts
*Attorney, Agent, or Firm*—Sherman & Shalloway

[57] ABSTRACT

A process for producing a steroid compound having an oxo group in the side chain, which comprises condensing an acid halide having a steroid skeleton with an organozinc compound at the halocarbonyl group of the acid halide in an inert organic medium in the presence of a catalytic amount of an ether capable of forming a complex with the organozinc compound, and if desired, hydrolyzing the product. The process produces the steroid compound at a high yield, and often at an almost quantitative yield. The steroid compound is an important intermediate for the production of vitamin $D_3$ analogs such as active forms of vitamin $D_3$. In one preferred embodiment, an industrially advantageous process from the standpoint of operation is provided.

13 Claims, No Drawings

PROCESS FOR PRODUCING STEROID COMPOUNDS HAVING AN OXO GROUP IN THE SIDE CHAIN

This invention relates to a process for producing steroid compounds having an oxo group in the side chain. More specifically, this invention relates to a process for producing steroid compounds having an oxo group in the side chain, which are useful intermediates convertible to vitamin $D_3$ analogs.

Steroid compounds having an oxo group in the side chain, such as 24-oxocholesterol, have previously been known as intermediates for the production of active vitamin $D_3$ such as $1\alpha,25$-dihydroxycholecalciferol and $1\alpha,24$-dihydroxycholecalciferol.

As described, for example, in The Journal of the American Chemical Society, 66, 723 (1944) and Japanese Laid-Open Patent Publication No. 42864/77, these steroid compounds having an oxo group in the side chain are known to be produced by the reaction between an acid chloride having a steroid nucleus and isopropylcadmium.

The Journal of the American Chemical Society, 66, 723 (1944) discloses an example in which 24-oxocholesterol was obtained in a yield of 46% by reacting $3\beta$-acetoxychol-5-enyl chloride with diisopropylcadmium in an ether solvent. Since, however, it is known that the diethyl ether used as a solvent reacts with the acid chloride to form the ethyl ester of the carboxylic acid as a by-product, thus decreasing the yield of the desired product, Example of Japanese Laid-Open Patent Publication No. 42864/77 discloses a method in which $3\alpha$-acetoxycholanyl chloride is reacted with diisopropyl-cadmium in a solvent obtained by adding benzene to ether used in the production of the diisopropylcadmium and distilling off the ether. In this reaction, the yield of the final product, $3\alpha$-hydroxy-24-oxo-$5\beta$-cholestane is only 48.4%. A tracing experiment conducted by the inventors of the present application has shown that the steriod compound having an oxo group in the side chain is obtained in much the same yield.

It is known on the other hand that the side-reaction of the acid halide with an ether as a solvent can be inhibited by using dibutyl ether as the solvent [see The Journal of the American Chemical Society, 68, 2078 (1946)]. Experiments of the present inventors, however, have shown that when $3\beta$-acetoxychol-5-enyl chloride is reacted with isopropyl zinc bromide in dibutyl ether as a solvent, the desired 24-oxocholesterol is obtained in a yield of as a small as 42 to 52%.

It is an object of this invention therefore to produce a steroid compound having an oxo group ($=$O) in the side chain at a high yield.

Another object of this invention is to produce a steroid compound having an oxo group in the side chain by a commercially advantageous method.

Other objects of this invention will become apparent from the following description.

These objects and advantages of this invention can be achieved by a process for producing a steroid compound having an oxo group in the side chain expressed by the formula

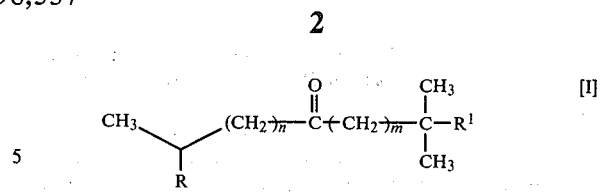

wherein R represents a steroid skeleton, $R^1$ represents a hydrogen atom, a hydroxyl group, or a hydroxyl group protected as an ether group, and n and m, independently from each other, represent 0 or an integer of 1 to 4, provided that when m is 0, $R^1$ is a hydrogen atom, which comprises condensing an acid halide of the formula

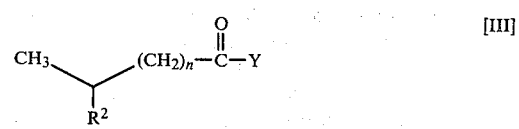

wherein $R^2$ represents the same or different steroid skeleton as or from R, n is as defined, and Y represents a halogen atom, with an organozinc compound of the formula

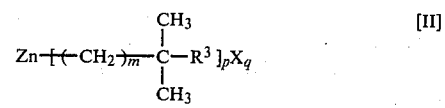

wherein $R^3$ represents a hydrogen atom or a hydroxyl group protected as an ether group, p is 1 or 2, and q is 0 or 1, provided that p+q=2, X represents a halogen atom, and m is as defined.

in an inert organic medium in the presence of a catalytic amount of an ether capable of forming a complex with the organozinc compound, and if desired, hydrolyzing the resulting product.

The acid halide used in this invention is expressed by formula [III] in which R represents a steroid skelton and Y represents a halogen atom such as chlorine, bromine or iodine, preferably chlorine or bromine. The steroid skeleton may, for example, be a gonane-, estrane- or androstane-type skeleton. The bonding between ring A and ring B in these steroid skeletons may be trans or cis.

Among such acid halides, androstanic acid halides of the formula

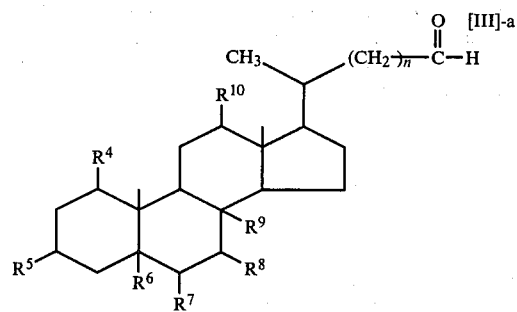

wherein $R^4$, $R^5$, $R^6$, $R^7$, $R^8$, $R^9$ and $R^{10}$, independently from each other, represent a hydrogen atom or a protected hydroxyl group $R^6$ and $R^7$, taken together, may form a carbon-carbon bond in which case $R^8$ and $R^9$, taken together, may further form a carbon-carbon bond, or R[5] and R[6], taken together, may form a carbon-carbon bond which R[7] may be a protected hydroxyl group,
are suitable intermediates for vitamin D3 analogs. Since they are comparatively easily available, they can be used as suitable starting materials in the method of this invention.

In formula [III]-a, R[4] through R[10], independently from each other, represent a hydrogen atom or a protected hydroxyl group. Compounds of formula [III]-a in which R[5], both R[5] and R[7], both R[5] and R[10], and all of R[5], R[8] and R[10] represent a protected hydroxyl group can be easily produced in a manner known per se from the corresponding naturally occurring substances having a free hydroxyl group. Examples of protective groups for the hydroxyl group include aliphatic carboxylic acid residues such as formyl, acetyl, propionyl and pivaloyl, aromatic carboxylic acid residues such as benzoyl, p-nitrobenzoyl, o-methylbenzoyl, and p-methoxybenzoyl, and groups forming an ether linkage such as benzyl, trityl, tetrahydropyranyl, β-ethoxyethyl, t-butyldimethylsilyl and trimethylsilyl.

R[6] and R[7], taken together, may form a carbon-carbon bond, in which case R[8] and R[9], taken together, may further form a carbon-carbon bond. In the former case, the double bond exists at the 5-position of the steroid nucleus, and in the latter case, two double bonds exist at the 5- and 7-positions of the steroid nucleus.

Or R[5] and R[6] may form a carbon-carbon double bond and simultaneously, R[7] may be a protected hydroxyl group.

The acid halide of formula [III]-a can be produced generally by reacting the corresponding carboxylic acid with a halogenating agent. The method is known per se, and disclosed, for example, in J. Pharm. Soc. (Japan), 57, 963 (1937).

Examples of the acid halide of formula [III] or [III]-a include 3β-acetoxychol-5-enyl halides, 3β-acetoxy-22,23-bisnor-chol-5-enyl halides, 3β-acetoxy-23-norchol-5-enyl halides, 3β-acetoxy-23a-homo-chol-5-enyl halides, cholanyl halides, 3α,6α-diacetoxycholanyl halides, 3α-acetoxycholanyl halides, 3β-acetoxychol-5,7-dienyl halides, and 6β-methoxy-3α,5-cyclo-5α-cholanyl halides. It should be understood that these exemplified halides are, for example, acid chlorides or acid bromides, and the acetoxy group as a protective group for the hydroxyl group is one example of a protective group for the hydroxyl group, and the corresponding acid halides in which the hydroxyl group is protected with the groups exemplified hereinabove are also exemplary of the acid halides of formula [III] or [III]-a.

The organozinc compound, the other starting material in the process of this invention, is expressed by the following formula [II].

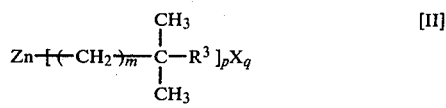

wherein R[3] represents a hydrogen atom or a hydroxyl group protected as an ether group, p is 1 or 2, q is 0 or 1, X represents a halogen atom, and m is 0 or an integer of 1 to 4, provided that p+q is equal to the valence of zinc.

The hydroxyl group protected as an ether group is, for example, a hydroxyl group protected with the protective groups exemplified hereinabove. X represents a halogen atom such as chlorine, bromine or iodine preferably chlorine or bromine.

The organozinc compound can be produced by reacting the corresponding zinc halide with a Grignard reagent, as described in detail hereinbelow.

Examples of the organozinc compound are Zn[CH(CH3)2]2, Zn[CH2CH(CH3)2]2, Zn[(CH2)2CH(CH3)2]2, Zn[(CH2)4CH(CH3)2]2 and

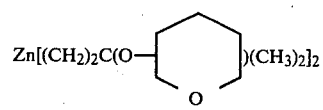

when p=2 and q=0; and Zn[CH(CH3)2]Br, Zn[CH(CH3)2]Cl, Zn[CH2CH(CH3)2]Br, Zn[CH2CH(CH3)2]Cl, Zn[(CH2)2CH(CH3)2]Br, Zn[(CH2)2CH(CH3)2]Cl, Zn[(CH2)3CH(CH3)2]Cl, Zn[(CH2)4CH(CH3)2]Br,

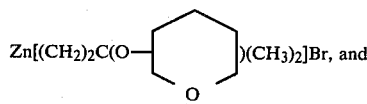

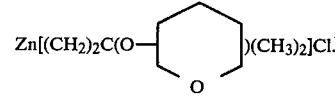

The process of this invention is carried out by condensing the acid halide of formula [III] with the organozinc compound of formula [II] in an inert organic medium in the presence of an ether capable of forming a complex with the organozinc compound.

Investigations of the present inventors have shown that the ethers which can be used in the process of this invention are limited to those capable of forming a complex with the organozinc compound. It is believed therefore that the reaction in accordance with this invention proceeds while the organozinc compound is forming a complex with the ether.

It is also necessary that the reaction in accordance with this invention should be carried out using the ether in a catalytic amount. It has been found that if the ether is present in too large an amount in the reaction system, the yield of the product decreases markedly beyond anticipation. Preferred ethers that can be used in the process of this invention are those having one etheric oxygen atom in the molecule. Examples of such ethers include aliphatic ethers having 2 to 10 carbon atoms such as dimethyl ether, methyl ether ether, diethyl ether, diisopropyl ether, dibutyl ether and diamyl ether, and 5- or 6-membered aliphatic ethers such as tetrahydrofuran and tetrahydropyran. These are merely illustrative, and the ethers that can be used in this invention are not limited to these specific examples.

According to this invention, the ether is used in an amount of generally not more than 3 moles, preferably 0.1 to 2 moles, especially preferably 0.3 to 1.5 moles, per mole of the organozinc compound used. The yield of the final product tends to decrease abruptly when the ether is used as a solvent or is used in an amount above the catalytic amount.

Stoichiometrically, 1 mole of the acid halide of formula [III] reacts with 1 mole (when p=1 and q=1 in formula [II]) or 0.5 mole (p=2 and q=0 in formula [II])

of the organozinc compound of formula [II]. In view of the rate of reaction, the yield of the final product and the reaction operation, it is generally desirable to use the organozinc compound in an amount of 2.5 to 50 moles, preferably 5 to 10 moles, per mole of the acid halide.

As the organozinc compund, a compound of formula [III] in which $p=1$ and $q=1$, a compound of formula [III] in which $p=2$ and $q=0$, and a mixture of these may be used. Generally, the compound of formula [II] in which $p=1$ and $q=1$ tends to give the desired product in a higher yield than the compound of formula [II] in which $p=2$ and $q=0$. The mixture of these gives a yield which is intermediate between those given by these two compounds depending upon the mixing ratio.

The inert organic medium is, for example, a compound which is liquid under the reaction conditions, desirably at room temperature. Examples of the inert organic medium are aromatic hydrocarbons such as benzene, toluene, xylene and mixed xylene, and aliphatic or alicyclic hydrocarbons such as petroleum ether, hexane, ligroin, cyclohexane and decalin. The term "inert" means that the medium does not react with the starting materials used in the process of this invention and the desired product.

The amount of the inert organic medium may be any amount which causes the reaction to proceed smoothly. Generally, it is 10 to 100 parts by weight, preferably 15 to 60 parts by weight, per part by weight of the acid halide used.

The reaction temperature varies depending upon the type and amount of the inert organic medium, the starting materials, etc. Generally, it is about $-20°$ C. to about $100°$ C., preferably $5°$ to $50°$ C., especially $10°$ to $15°$ C.

Thus, according to the process of this invention, there is obtained a steroid compound of the formula

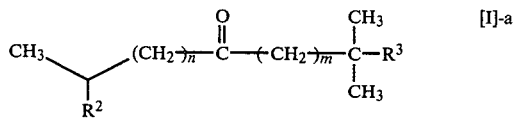

having an oxo group in the side chain and optionally having a protected hydroxyl group.

In formula [I]-a, $R^2$, $R^3$, m and n are as defined. Specifically, $R^2$ is a steroid skeleton optionally having a protected hydroxyl group, and $R^3$ is a hydrogen atom or a hydroxyl group protected as an ether group. The protective groups for the hydroxyl group are as exemplified hereinabove.

According to one especially preferred embodiment of the process of this invention, it has been found that the final desired product can be obtained at a particularly high yield, and at times, at almost quantitative yields, by using an organozinc compound of the formula

wherein X, p and q are as defined hereinabove, in which the carbon atom to be bonded with the carbonyl group of the acid halide is a secondary carbon atom. This preferred embodiment is also advantageous in that it permits the production of a steroid compound having 8 carbon atoms in the side chain, which is an important intermediate for a vitamin $D_3$ analog, by using a hydroxy-protected type acid halide of commercially available 3$\beta$-hydroxychol-5-enic acid (cholenic acid).

According to another especially preferred embodiment of the process of this invention, the final desired product can equally be obtained in a high yield by performing the condensation reaction in the substantial absence of water. It is recommended therefore that the reaction medium and ether which are most likely to bring water to the reaction system should be subjected to a dehydration treatment in a manner known per se prior to use. The presence of water can substantially be excluded, for example, by treating the hydrocarbon medium with metallic sodium, or by treating it with tetrahydrofuran or anhydrous calcium sulfate and further treating it with lithium aluminum hydride at the time of distillation.

Isolation and purification of the desired steroid compound in the process of this invention can be performed in a method known per se, which, for example, comprises directly treating the reaction product mixture with a mineral acid, treating the organic layer with a saturated aqueous solution of sodium chloride, dehydrating the treated mass with anhydrous magnesium sulfate, concentrating the dried product, and if desired, purifying the residue (crude product) by recrystallization or column chromatography.

Since, however, according to the process of this invention, the aforesaid steroid compound is obtained in an almost quantitative yield, and the hydroxyl group is desirably in free from for use as a starting material for vitamin $D_3$ analogs, it is also possible to obtain the desired product by directly hydrolyzing the reaction product mixture as obtained by the condensation reaction.

The hydrolysis can be performed by a method known per se which, for example, comprises heating the concentration residue (crude product) obtained by the above isolating and purifying procedure for example at a temperature of, for example, $40°$ C. to $80°$ C. together with an alkaline alcohol such as $KOH/CH_3OH$ with stirring, after optionally adding a solvent such as benzene in order to increase the solubility of the residue.

The isolation and purification of the hydrolysis product can be performed in a method known per se which, for example, comprises adding water to the resulting reaction mixture, extracting it with an organic medium such as benzene, washing the extract with a mineral acid, treating it with a saturated aqueous solution of sodium bicarbonate, treating it further with a saturated aqueous solution of sodium chloride, dehydrating the treated product with anhydrous sodium sulfate, concentrating it, and if desired, purifying the concentrate by recrystallization or chromatography.

In the manner described hereinabove, a steroid compound having an oxo group in the side chain and expressed by the following formula

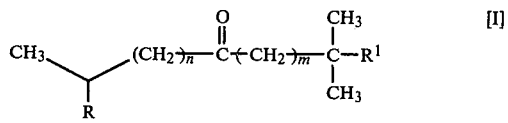

wherein R, $R^1$, m an n are as defined above, is obtained.

As is already apparent, in formula [I], R is a steroid skeleton which may contain a hydroxyl group or a protected hydroxyl group, and $R^1$ is a hydrogen, a hydroxyl group, or a protected hydroxyl group.

Examples of the steroid compound of formula [I] include
3β-hydroxy-24-oxocholest-5-ene (24-oxocholesterol),
3β-acetoxy-24-oxocholest-5-ene,
3β-hydroxy-22-oxocholest-5-ene,
3β,25-dihydroxy-22-oxocholest-5-ene,
3β-hydroxy-23-oxocholest-5-ene,
3β-hydroxy-24-nor-23-oxocholest-5-ene,
3β-hydroxy-24a-homo-24a-oxocholest-5-ene,
24-oxo-5β-cholestane,
24-oxo-24a-homo-5β-cholestane,
3α,6α-dihydroxy-24-oxo-5β-cholestane,
3α,6α-diacetoxy-24-oxo-5β-cholestane,
3α,6α-diacetoxy-24-oxo-24a-homo-5β-cholestane,
3α,6α-dihydroxy-24-oxo-24a,24b-bis-homo-5β-cholestane,
3α-hydroxy-24-oxo-5β-cholestane,
3α-acetoxy-24-oxo-5β-cholestane,
3α-benzoyloxy-24-oxo-5β-cholestane,
3α-ethoxycarbonyloxy-24-oxo-5β-cholestane,
3α-hydroxy-24-oxo-24a-homo-5β-cholestane,
3α-hydroxy-24-oxo-24a,24b-bis-homo-5β-cholestane,
3β-hydroxy-24-oxocholesta-5,7-diene,
3β-acetoxy-24-oxocholesta-5,7-diene,
1α,3β-dihydroxy-24-oxocholesta-5,7-diene,
1α,3β-diacetoxy-24-oxocholesta-5,7-diene, and
6β-methoxy-3α,5-cyclo-24-oxo-5α-cholestane.

The present invention, in another aspect, provides a combined process for producing a steroid compound of general formula [I], which comprises preparing an organozinc compound of formula [II] from a Grignard reagent, adding an acid halide of formula [III] directly to the resulting reaction mixture, allowing a condensation reaction between the organozinc compound and the acid halide to take place, and if desired, hydrolyzing the reaction product.

This combined process is industrially advantageous in that the reaction mixture resulting in the production of the Grignard reagent can be directly used in a subsequent step of performing the condensation reaction between the organozinc compound and the acid halide. This is in contrast, for example, to the method disclosed in Japanese Laid-Open Patent Publication No. 42864/77 in which the solvent used in the production of the Grignard reagent is removed on the ground that it induces a side-reaction in the subsequent condensation reaction, and thus, the subsequent condensationn reaction is carried out in a solvent freshly supplied.

More specifically, this combined process in accordance with this invention comprises performing an addition reaction between metallic magnesium and an alkyl halide of the following formula

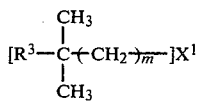   [IV]

wherein $R^3$ and m are as defined hereinabove and $X^1$ represents a halogen atom,
in the presence of an ether in an inert organic medium to obtain a mixture containing an organomagnesium compound of the formula

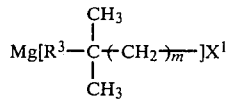   [V]

wherein $R^3$, $X^1$ and m are as defined above;
adding a zinc halide of the formula $$Zn(X^2)_2 \quad [VI]$$

wherein $X^2$ represents a halogen atom,
to the resulting mixture to obtain a mixture containing an organozinc compound of the formula

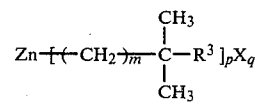   [II]

wherein $R^3$, m, p and q are as defined hereinabove, and
X represents a halogen atom represented by $X^1$ or $X^2$,
and a catalytic amount of the ether capable of forming a complex with the organozinc compound, adding an acid halide of the formula

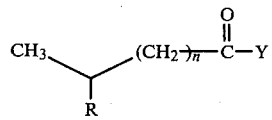   [III]

wherein R, Y and n are as defined above,
to perform the condensation reaction between the organozinc compound and the acid halide, and if desired, hydrolyzing the resulting product, thereby forming the steroid compound of formula [I] having an oxo group in the side chain.

In the above process, the first step comprises an addition reaction between the alkyl halide of formula [IV] and metallic magnesium in an inert organic medium in the presence of an ether.

Examples of the alkyl halide are isopropyl bromide, isopropyl chloride, isobutyl bromide, isoamyl bromide, isoamyl chloride, 2,2-dimethyl-2-tetrahydropyranyloxyethyl chloride and 3,3-dimethyl-3-(β-ethoxyethyloxy)-propyl bromide.

The ether used as a catalyst and the inert organic medium may be the same as those exemplified hereinabove. The ether used in the first step needs not always to be capable of forming a complex with the organozinc compound formed in the second step [see Chemistry and Industry, p. 426 (1965)]. However, in the process of this invention, ethers having such a property are used.

The amount each of the alkyl halide and metallic magnesium is preferably 5 to 50 moles per mole of the acid halide used in the third step.

The amount of the ether is preferably 0.1 to 2 moles, especially preferably 0.3 to 1.5 moles, per mole of the metallic magnesium.

The reaction temperature is preferably 15° to 80° C., especially preferably 40° to 50° C.

Thus, by the first step, a mixture containing the organomagnesium compound of formula [V] is obtained.

The second reaction step comprises added the zinc halide of formula [VI] to the mixture containing the organomagnesium compound of formula [V], and reacting the zinc halide with the organomagnesium compound in the inert organic medium in the presence of the ether.

Zinc bromide, zinc chloride and zinc iodide, for example, are used as the zinc halide. Zinc bromide is preferred.

The amount of the zinc halide is 2.5 to 250 moles, preferably 2.5 to 50 moles, per mole of the acid halide used in the third step. When the zinc halide is used in too large an amount, the reaction system undesirably tends to form a heavy slurry.

The reaction temperature is generally 15° to 80° C., preferably 55° to 65° C.

Thus, the second step affords a mixture containing the organozinc compound of formula [II] and a catalytic amount of the ether used in the first step capable of forming a complex with the organozinc compound.

X in formula [II], $X^1$ in formula [IV], and $X^2$ in formula [VI] all represent a halogen atom.

According to the third step, the acid halide of formula [III] is added to the resulting reaction mixture either as such or as a solution in an inert organic medium, and the reaction between the acid halide and the organozinc compound described in detail hereinabove is carried out in the presence of a catalytic amount of the ether.

After the reaction, the reaction mixture is hydrolyzed, if desired, and the reaction product is isolated and purified. Thus, the desired steroid compound of formula [I] having an oxo group in the side chain can be obtained in a high yield, and at times, almost in a quantitative yield.

The resulting steroid compound can be converted to a pharmacologically active vitamin $D_3$ analog in a known manner. For example, 24-oxocholesterol of the formula

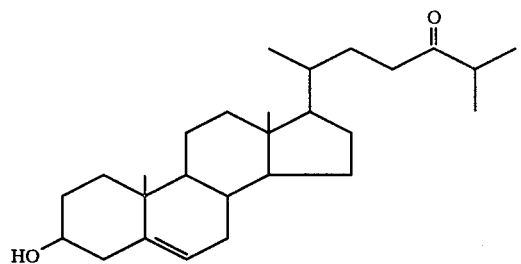

obtained by the process of this invention can be converted to 1α,24-dihydroxycholecalciferol of the formula

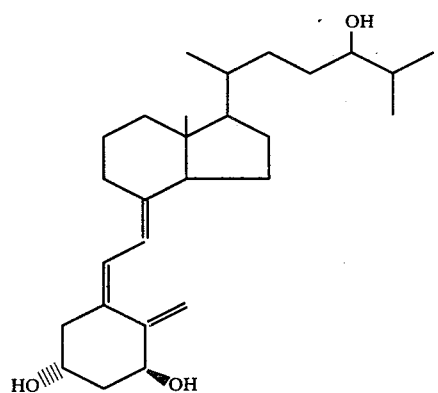

having superior pharmacological activity by converting it to 1α,24-dihydroxycholesterol by the known method of D. H. R. Barton et al. [see The Journal of the American Chemical Society, 95, 2748 (1973)], preparing the corresponding 5,7-diene from it in a known manner, and thermally isomerizing it by the irradiation of light (see, for example, U.S. Pat. No. 4,022,891).

The following examples illustrate the process of this invention in greater detail. These examples are merely illustrative, and should not be construed as limiting the invention.

EXAMPLE 1

Production of 3β-hydroxy-24-oxocholest-5-ene:

(a) Production of 3β-acetoxychol-5-enyl chloride:

3β-Acetoxychol-5-enic acid (4.16 g; 10 mmoles) was added to 60 ml of anhydrous benzene. The solution was cooled with ice, and with stirring, 4.5 ml of thionyl chloride was gradually added dropwise. After the addition, the mixture was stirred at room temperature for 2.5 hours. The reaction mixture was concentrated under reduced pressure, and to the resulting residue was added 20 ml of anhydrous benzene which had been obtained by dehydrating benzene with sodium. The mixture was repeatedly concentrated under reduced pressure to remove the thionyl chloride contained in the residue. The resulting crude solid product, 3β-acetoxychol-5-enyl chloride, was used as a starting compound in the subsequent step without purification.

(b) Production of 3β-hydroxy-24-oxocholest-5-ene:

(i) Magnesium flakes (1.9 g; 78.8 mmoles) and 6.4 ml (78.8 mmoles) of anhydrous tetrahydrofuran were added to 40 ml of anhydrous benzene. The resulting suspension was heated on a warm bath at 45° C. With stirring, a solution of 7.0 ml (75 mmoles) of isopropyl bromide in 40 ml of anhydrous benzene was added dropwise, and after the addition, the mixture was stirred under heat to dissolve magnesium completely.

(ii) The solution was cooled, and then 16.9 g (75 mmoles) of a powder of anhydrous zinc bromide was added. The mixture was heated at a bath temperature of 55° C. for 2 hours with stirring.

(iii) The solution was cooled, and with ice cooling (5° C.) and stirring, 30 ml of a solution of the crude 3β-acetoxychol-5-enyl chloride in an anhydrous benzene was added dropwise. After the addition, the mixture was stirred at room temperature for 1 hour, and further 50 ml of cold water and 17 ml of 6 N hydrochloric acid were added dropwise to terminate the reaction.

After the reaction, water and benzene were added to separate the reaction mixture into layers. The aqueous layer was extracted with benzene. The benzene extract was combined with the benzene layer, and the mixture was washed with a saturated aqueous solution of sodium chloride, dried over anhydrous magnesium sulfate, filtered, and concentrated. The resulting solid crude product, 3β-acetoxy-24-oxocholest-5-ene, without purification, was subjected to a hydrolysis reaction.

Specifically, the crude 3β-acetoxy-24-oxocholest-5-ene was dissolved in 100 ml of a mixture of methanol and benzene (1:1). To the solution was added dropwise a 10% methanol solution of potassium hydroxide at room temperature with stirring. After the addition, the mixture was stirred at 70° C. for 4 hours. After the reaction, 100 mg of water was added to separate the reaction mixture into layers. The resulting aqueous layer was extracted twice with benzene. The benzene extracts were combined with the organic layer. The mixture was washed successively with dilute hydrochloric acid, a saturated aqueous solution of sodium bicarbonate, and a saturated aqueous solution of sodium chloride, dried over anhydrous sodium sulfate, filtered, and concentrated to form 3.6 g (yield: 90% based on 3$\beta$-acetoxychol-5-enic acid) of 3$\beta$-hydroxy-24-oxocholest-5-ene as a white solid. The properties of the product were as follows:

Melting point: 135°–136° C.

IR (KBr)cm$^{-1}$: 3450, 2945, 1708, 1465, 1375.

NMR (CDCl$_3$, TMS), $\delta$(ppm): 0.67 (3H, s, C-18-CH$_3$), 0.91 (1H, d, J=6 Hz, C-25-H), 1.01 (3H, s, C-19-CH$_3$), 1.09 (6H, d, J=6 Hz, C-26-CH$_3$, C-27-CH$_3$), 1.59 (1H, s, C-3-OH), 3.52 (1H, bm C-3-H), 5.32 (1H, bd, C-6-H).

EXAMPLE 2

Example 1 was repeated except that 8.1 ml of diethyl ether was used instead of 6.4 ml of tetrahydrofuran in Example 1. There was obtained 3.3 g (yield 8.25%) of 3$\beta$-hydroxy-24-oxocholest-5-ene.

COMPARATIVE EXAMPLE 1

Example 1 was repeated except that 10.6 g of ethylene glycol dimethyl ether was used instead of 6.4 ml of tetrahydrofuran in Example 1. Formation of the desired 3$\beta$-hydroxy-24-oxocholest-5-ene could not be ascertained.

It was judged from the result that ethylene glycol dimethyl ether cannot be used as the ether in the process of this invention.

COMPARATIVE EXAMPLE 2

Example 1 was repeated except that 10.6 g of dioxane was used instead of 6.4 ml of tetrahydrofuran in Example 1. There was obtained only 0.2 g (yield 5%) of 3$\beta$-hydroxy-24-oxocholest-5-ene.

It was judged from the result that dioxane can neither be used as the ether in the process of this invention.

EXAMPLE 3

Example 1 was repeated except that the amount of the tetrahydrofuran was changed to 3.4 ml. There was obtained 2.5 g (yield 62.5%) of 3$\beta$-hydroxy-24-oxocholest-5-ene.

COMPARATIVE EXAMPLE 3

Example 1 was repeated except that the amount of the tetrahydrofuran was changed to 68.4 ml. There was obtained only 0.2 g (yield 5%) of the desired 3$\beta$-hydroxy-24-oxocholest-5-ene.

It is seen from the result that the presence of too much ether in the reaction system inhibits the reaction even if the ether is the one that can be used in the process of this invention.

EXAMPLE 4

Example 1 was repeated except that toluene was used as a reaction medium instead of benzene in the same amount. There was obtained 3.1 g (yield 77.5%) of 3$\beta$-hydroxy-24-oxocholest-5-ene.

EXAMPLE 5

Example 1 was repeated except that xylene was used as a reaction medium instead of the benzene in the same amount. There was obtained 2.9 g (yield 72.5%) of 3$\beta$-hydroxy-24-oxocholest-5-ene.

EXAMPLE 6

Example 1 was repeated except that the amount of the anhydrous zinc bromide was changed to 12.7 g (56.25 mmoles). There was obtained 2.5 g (yield 62.5%) of 3$\beta$-hydroxy-24-oxocholest-5-ene.

EXAMPLE 7

Production of 3$\alpha$,6$\alpha$-dihydroxy-24-oxo-5$\beta$-cholestane:

(a) Production of 3$\alpha$,6$\alpha$-diacetoxycholanyl chloride (hyodeoxycholyl chloride-3$\alpha$,6$\alpha$-diacetate---starting compound)

Hyodeoxycholic acid-3$\alpha$,6$\alpha$-diacetate (14 g; 29.4 mmoles) was added to 200 ml of anhydrous benzene. The solution was cooled with ice, and with stirring, 15 ml of thionyl chloride was added dropwise. After the addition, the mixture was reacted at room temperature for 3.5 hours with stirring. The reaction mixture was concentrated under reduced pressure. To the residue was added 60 ml of anhydrous benzene, and the mixture was repeatedly concentrated under reduced pressure to remove the thionyl chloride contained in the residue. The resulting solid crude product, hyodeoxycholyl chloride-3$\alpha$,6$\alpha$-diacetate, was used as a starting compound in the subsequent step without purification.

(b) Production of 3$\alpha$,6$\alpha$-dihydroxy-24-oxo-5$\beta$-cholestane (i) Magnesium flakes (5.6 g; 232 mmoles) and 18.8 ml (232 mmoles) of anhydrous tetrahydrofuran were added to 120 ml of anhydrous benzene. The resulting suspension was heated at a bath temperature of 45° C. With stirring, a solution of 20.6 ml (220 mmoles) of isopropyl bromide in 120 ml of anhydrous benzene was added dropwise. After the addition, the solution was stirred for 2 hours under heat to dissolve magnesium completely.

(ii) The solution was cooled, and 49.6 g (220 mmoles) of a powder of anhydrous zinc bromide was added. Then, the mixture was heated at a bath temperature of 55° C. for 2 hours with stirring.

(iii) The mixture was cooled, and with ice cooling (5°C.) and stirring, 100 ml of a solution of the crude hyodeoxycholyl chloride-3$\alpha$,6$\alpha$-diacetate in anhydrous benzene was added dropwise. After the addition, the mixture was stirred at room temperature for 1 hour, and 100 ml of cold water and 50 ml of 6 N hydrochloric acid were added dropwise to terminate the reaction. After the reaction, water and benzene were added to separate the reaction mixture into layers. The aqueous layer was extracted with benzene. The benzene extract was combined with the benzene layer. The mixture was washed with an aqueous solution of a saturated aqueous solution of sodium chloride, dried over anhydrous magnesium sulfate, filtered, and concentrated. The resulting solid crude product, 3$\alpha$,6$\alpha$-diacetoxy-24-oxo-5$\beta$-cholestane was subjected to a hydrolysis reaction without purification.

Specifically, the crude 3$\alpha$,6$\alpha$-diacetoxy-24-oxo-5$\beta$-cholestane was dissolved in a mixture of methanol and benzene (1:1). To the solution was added dropwise a 10% methanol solution of potassium hydroxide at room temperature with stirring. After the addition, the mixture was stirred at 70° C. for 4 hours. After the reaction, 500 ml of water was added to separate the reaction mixture into layers. The aqueous layer was extracted twice with dichloromethane. The dichloromethane extracts were combined with the organic layer. The mixture was washed successively with dilute hydrochloric acid, a saturated aqueous solution of sodium bicarbonate and a saturated aqueous solution of sodium chloride, dried over anhydrous sodium sulfate, filtered, and concentrated to produce 9.0 g (yield: 73% based on the hyodeoxycholic acid-3α,6α-diacetate) of 3α,6α-dihydroxy-24-oxo-5β-cholestane as a white solid. The properties of the product were as follows:

Melting point: 182°–183° C. (recrystallized from methylene chloride/ethyl acetate).

IR (KBr, cm$^{-1}$): 3375, 2925, 2860, 1710, 1460, 1376.

NMR (CDCl$_3$, TMS), δ(ppm): 0.64 (3H, s, C-18-CH$_3$), 0.91 (3H, s, C-19-CH$_3$), 1.10 (6H, d, J=6 Hz, C-26-CH$_3$ and C-27-CH$_3$), 1.54 (2H, s, C-3-OH, C-6-OH), 3.63, 4.04 (each 1H, bm, C-3-H and C-6-H).

High resolution mass spectrum (70 eV): M$^+$ 418.3442 (C$_{27}$H$_{46}$O$_3$).

EXAMPLE 8

Production of 3α-hydroxy-24-oxo-5β-cholestane (a) Production of 3α-acetoxy-5β-cholanyl chloride (starting compound)

3α-Acetoxy-5β-cholanic acid (4.18 g; 10 mmoles) was added to 60 ml of anhydrous benzene. The solution was cooled with ice, and with stirring, 4.5 ml of thionyl chloride was gradually added dropwise. After the addition, the mixture was reacted at room temperature for 2.5 hours with stirring. The reaction mixture was concentrated under reduced pressure, and 20 ml of anhydrous benzene was added to the residue. The mixture was repeatedly concentrated under reduced pressure to remove the thionyl chloride contained in the residue. The resulting solid crude product, 3α-acetoxy-5β-cholanyl chloride, was used as a starting compound in the subsequent step without purification.

(b) Production of 3α-hydroxy-24-oxo-5β-cholestane (i) Magnesium flakes (1.9 g; 78.8 mmoles) and 6.4 ml (78.8 mmoles) of anhydrous tetrahydrofuran were added to 40 ml of anhydrous benzene. The resulting suspension was heated at a bath temperature of 45° C., and with stirring, a solution of 7.0 ml (75 mmoles) of isopropyl bromide in 40 ml of anhydrous benzene was added dropwise. After the addition, the mixture was heated for 2 hours with stirring to dissolve the magnesium completely.

(ii) The solution was cooled, and 16.9 g (75 mmoles) of a powder of anhydrous zinc bromide was added. The mixture was heated at a bath temperature of 55° C. for 2 hours with stirring.

(iii) The mixture was cooled. With ice cooling (5° C.) and stirring, 30 ml of a solution of the 3α-acetoxy-5β-cholanyl chloride in anhydrous benzene was added dropwise. After the addition, the mixture was stirred at room temperature for 1 hour, and further 100 ml of cold water and 50 ml of 6 N hydrochloric acid were added to terminate the reaction. After the reaction, suitable amounts of water and benzene were added to separate the reaction mixture into layers. The aqueous layer was extracted with benzene. The benzene extract was combined with the benzene layer. The mixture was washed with a saturated aqueous solution of sodium chloride, dried over anhydrous magnesium sulfate, filtered, and concentrated. The resulting solid crude product, 3α-acetoxy-24-oxo-5β-cholestane, was subjected to a hydrolysis reaction without purification. Specifically, the crude 3α-acetoxy-24-oxo-5β-cholestane was dissolved in a mixture of methanol and benzene (1:1), and a 10% methanol solution of sodium hydroxide was added dropwise to the resulting solution. After the addition, the solution was stirred at 70° C. for 4 hours. After the reaction, 100 ml of water was added to separate the reaction mixture into layers. The aqueous layer was extracted twice with benzene. The organic layer was combined with the benzene extract. The mixture was washed successively with dilute hydrochloric acid, a saturated aqueous solution of sodium bicarbonate and a saturated aqueous solution of sodium chloride, dried over anhydrous sodium sulfate, filtered, and concentrated to afford 2.95 g (yield 73% based on the 3α-acetoxy-5β-cholanic acid) of 3α-hydroxy-24-oxo-5β-cholestane as a white solid. The properties of this product were as follows:

IR (KBr. cm$^{-1}$): 3450, 2970, 2900, 1720, 1475, 1460, 1390, 1050.

NMR (CDCl$_3$, TMS), δ(ppm): 0.65 (3H, s, C-18-CH$_3$), 0.92 (3H, s, C-19-CH$_3$), 1.09 (6H, d, J=6 Hz, C-26-CH$_3$ and C-27-CH$_3$)., 3.60 (1H, bm, C-3-H).

High-resolution mass spectrum (70 eV): M$^+$ 402.3524 (C$_{27}$H$_{46}$O$_2$).

EXAMPLE 9

Production of 3β-hydroxy-24-oxo-24a-homocholest-5-ene

Magnesium flakes (380 mg; 15.76 mmoles) and 1.28 ml (15.76 mmoles) of anhydrous tetrahydrofuran were added to 8 ml of anhydrous benzene. To the resulting suspension was added dropwise a solution of 2.06 g (15 mmoles) of isobutyl bromide in 8 ml of anhydrous benzene with stirring at room temperature. After the addition, the mixture was stirred for 0.5 hour to dissolve the magnesium completely.

The solution was cooled, and 3.38 g (15 mmoles) of a powder of anhydrous zinc bromide was added. The mixture was heated at a bath temperature of 55° C. for 2 hours with stirring, and cooled. With ice cooling (5° C.) and stirring, 6 ml of a solution in anhydrous benzene of crude 3β-acetoxychol-5-enyl chloride obtained in the same way as in Example 1, (a) using 832 mg (2 mmoles) of 3β-acetoxychol-5-enic acid was added dropwise. After the addition, the mixture was stirred at room temperature for 1 hour, and 10 ml of cold water and 4 ml of 6 N hydrochloric acid were added to terminate the reaction.

After the reaction, suitable amounts of water and benzene were added to separate the reaction mixture into layers. The aqueous layer was extracted with benzene. The benzene extract was combined with the benzene layer. The mixture was washed with a saturated aqueous solution of sodium chloride, dried over anhydrous magnesium sulfate, filtered, and concentrated. The resulting solid crude product, 3β-acetoxy-24-oxo-24a-homocholest-5-ene was subjected to a hydrolysis reaction without purification. Specifically, the crude 3β-acetoxy-24-oxo-24a-homocholest-5-ene was dissolved in a mixture of methanol and benzene (1:1). A 10% methanol solution of potassium hydroxide was added dropwise to the solution with stirring at room temperature. After the addition, the solution was stirred at 70° C. for 4 hours. After the reaction, 100 ml of water was added to separate the reaction mixture into layers.

The aqueous layer was extracted twice with benzene. The benzene extracts were combined with the organic layer. The mixture was washed successively with dilute hydrochloric acid, a saturated aqueous solution of sodium bicarbonate and a saturated aqueous solution of sodium chloride, dried over anhydrous sodium sulfate, filtered, and concentrated to afford 662 mg (yield 80% based on the 3β-acetoxychol-5-enic acid) of 3β-hydroxy-24-oxo-24a-homocholest-5-ene as a white solid. The properties of the product were as follows:

IR (KBr, cm$^{-1}$): 2950, 1715, 1475, 1375, 1060.

NMR (CDCl$_3$, TMS), δ(ppm): 0.68 (3H, s, C-18-CH$_3$), 0.92 (6H, d, J=6 Hz, C-26-CH$_3$, C-27-CH$_3$), 1.01 (3H, s, C-19-CH$_3$), 3.50 (1H, bm, C-3-H), 5.32 (1H, bm, C-6-H).

High-resolution mass spectrum (70 eV): M$^+$ 414.3502 (C$_{28}$H$_{46}$O$_2$).

EXAMPLE 10

Production of 3β-hydroxy-24-oxo-24-a, 24b-bishomocholest-5-ene

Magnesium flakes (380 mg; 15.76 mmoles) and 1.28 ml (15.76 mmoles) of anhydrous tetrahydrofuran were added to 8 ml of anhydrous benzene. To the resulting suspension was added dropwise a solution of 2.27 g (15 mmoles) of isoamyl bromide in 8 ml of anhydrous benzene with stirring at room temperature. After the addition, the mixture was stirred for 0.5 hour to dissolve the magnesium completely. The solution was cooled, and 3.38 g (15 mmoles) of a powder of anhydrous zinc bromide was added. The mixture was heated at a bath temperature of 55° C. with stirring, and then cooled. With ice cooling (5° C.) and stirring, 6 ml of a solution in anhydrous benzene of crude 3β-acetoxychol-5-enyl chloride obtained in the same way as in Example 1, (a) using 832 mg (2 mmoles) of 3β-acetoxychol-5-enic acid was added dropwise. After the addition, the mixture was stirred at room temperature for 1 hour. Cold water (10 ml) and 4 ml of 6 N hydrochloric acid were added dropwise to terminate the reaction.

After the reaction, suitable amounts of water and benzene were added to separate the reaction mixture into layers. The aqueous layer was extracted with benzene. The benzene extract was combined with the benzene layer. The mixture was washed with a saturated aqueous solution of sodium chloride, dried over anhydrous magnesium, filtered, and concentrated. The resulting solid crude product, 3β-acetoxy-24-oxo-24a, 24b-bishomocholest-5-ene, was subjected to a hydrolysis reaction without purification.

Specifically, the crude 3β-acetoxy-24-oxo-24a, 24b-bishomocholest-5ene was dissolved in 20 ml of a mixture of methanol and benzene (1:1), and to the solution was added dropwise a 10% methanol solution of potassium hydroxide. After the addition, the mixture was stirred at 70° C. for 4 hours. After the reaction, 100 ml of water was added to separate the reaction mixture into layers. The aqueous layer was extracted twice with benzene. The benzene extracts were combined with the organic layer. The mixture was washed with dilute hydrochloric acid, a saturated aqueous solution of sodium bicarbonate and a saturated aqueous solution of sodium chloride, dried over anhydrous sodium sulfate, filtered, and concentrated to afford 678 mg (yield 79% based on the 3β-acetoxychol-5-enic acid) of 3β-hydroxy-24-oxo-24a, 24b-bishomocholest-5-ene as a white solid. The properties of the product were as follows:

IR (KBr, cm$^{-1}$): 3470, 2970, 1720, 1475, 1380, 1060.

NMR (CDCl$_3$, TMS), δ(ppm): 0.68 (3H, s, C-18-CH$_3$), 0.92 (6H, d, J=6 Hz, C-26-CH$_3$, C-27-CH$_3$), 1.01 (3H, s, C-19-CH$_3$), 3.50 (1H, bm, C-3-H), 5.31 (1H, br, C-6-H).

High-resolution mass spectrum (70 eV): M$^+$ 428.3638 (C$_{29}$H$_{48}$O$_2$).

EXAMPLE 11

Production of 3β-hydroxy-24-oxo-cholest-5-ene (a) Production of 3β-acetoxychol-5-enyl chloride (starting compound)

3β-Acetoxychol-5-enic acid (500 g; 1.2 moles) was added to 8 liters of anhydrous benzene obtained by dehydration with a molecular sieve. The resulting solution was cooled with ice, and with stirring, 390 ml (5.4 moles) of thionyl chloride was added dropwise. After the addition, the mixture was stirred at room temperature for 4 hours. The reaction mixture was concentrated under reduced pressure, and 2 liters of anhydrous benzene resulting from dehydration with a molecular sieve was added to the residue. The mixture was repeatedly concentrated under reduced pressure (five times) to remove the thionyl chloride contained in the residue. The resulting solid crude product, 3β-acetoxychol-5-enyl chloride, was used in the subsequent step as a starting compound without purification.

(b) Production of 3β-hydroxy-24-oxocholest-5-ene (i) Magnesium flakes (219 g; 9.0 moles) and 681 g (9.4 moles) of anhydrous tetrahydrofuran were added to 8 liters of anhydrous benzene resulting from dehydration with a molecular sieve. The resulting suspension was heated at a bath temperature of 50° to 55° C., and with stirring, a solution of 1 kg (8.1 moles) of isopropyl bromide in 3 liters of anhydrous benzene was added dropwise. After the addition, the mixture was heated for 2 hours with stirring to dissolve the magnesium.

(ii) The solution was cooled, and 2.2 kg (9.8 moles), of a powder of anhydrous zinc bromide was added. Then, the mixture was heated at a bath temperature of 55° C. for 2 hours with stirring.

(iii) The mixture was cooled, and with ice cooling (5° C.) and stirring, a solution of the crude 3β-acetoxychol-5-enyl chloride in 6 liters of anhydrous benzene was added dropwise. After the addition, the mixture was stirred at room temperature for 1 hour, and further, 3 liters of cold water and 1.2 liters of 6 N hydrochloric acid were added dropwise to terminate the reaction. After the reaction, water and benzene were added to separate the reaction mixture into layers. The aqueous layer was extracted with benzene. The benzene extract was combined with the benzene layer. The mixture was washed with a saturated aqueous solution of sodium chloride, dried over anhydrous magnesium sulfate, filtered, and concentrated.

The resulting solid crude product, 3β-acetoxy-24-oxocholest-5-ene, was subjected to a hydrolysis reaction without purification.

Specifically, the crude 3β-acetoxy-24-oxocholest-5-ene was dissolved in 7.2 liters of a mixture of methanol and benzene (1:1). With stirring at room temperature, 3.6 liters of a 10% methanol solution of potassium hydroxide was added dropwise. After the addition, the mixture was stirred at 70° C. for 6 hours.

After the reaction, water was added to separate the reaction mixture into layers. The aqueous layer was extracted twice with benzene. The benzene extracts were combined with the organic layer. The mixture was washed successively with dilute hydrochloric acid, a saturated aqueous solution of sodium bicarbonate and a saturated aqueous solution of sodium chloride, dried over anhydrous sodium sulfate, filtered, and concentrated to afford 369 g (yield 77% based on the 3β-acetoxychol-5-enic acid) of 3β-hydroxy-24-oxocholest-5-ene as a white solid.

COMPARATIVE EXAMPLE 4

Method involving the use of an organocadmium compound and a catalytic amount of an ether (i) Magnesium flakes (1.9 g; 78.8 mmoles) and 6.4 ml (78.8 mmoles) of anhydrous tetrahydrofuran were added to 40 ml of anhydrous benzene. The resulting suspension was heated at a bath temperature of 45° C., and with stirring, a solution of 7.0 ml (75 mmoles) of isopropyl bromide in 40 ml of anhydrous benzene was added dropwise. After the addition, the mixture was heated for 2 hours with stirring to dissolve magnesium completely.

(ii) The solution was cooled, and 20.4 g (75 mmoles) of a powder of anhydrous cadmium bromide was added. The mixture was heated at a bath temperature of 55° C. with stirring, and then cooled to prepare a benzene solution of the isopropylcadmium compound.

(iii) With ice cooling (5° C.) and stirring, 30 ml of a solution in anhydrous benzene of 3β-acetoxychol-5-enyl chloride obtained in the same way as in Example 1, (a) using 4.16 g (10 mmoles) of 3β-acetoxychol-5-enic acid was added dropwise to the benzene solution prepared in (ii). After the addition, the mixture was stirred at room temperature for 1 hour, and 50 ml of cold water and 17 ml of 6 N hydrochloric acid were added dropwise to terminate the reaction.

After the reaction, suitable amounts of water and benzene were added to separate the reaction mixture into layers. The aqueous layer was extracted with benzene. The benzene extract was combined with the benzene layer. The mixture was washed with a saturated aqueous solution of sodium chloride, dried over anhydrous magnesium sulfate, filtered, and concentrated. The resulting crude solid product, 3β-acetoxy-24-oxocholest-5-ene, was subjected to a hydrolysis reaction in the same way as in Example 1 without purification. The product was isolated and purified to provide 1.84 g (yield 46% based on the 3β-acetoxychol-5-enic acid) of 3β-hydroxy-24-oxocholest-5-ene.

The product had the same properties as those shown in Example 1.

COMPARATIVE EXAMPLE 5

Conventional process involving the use of an organocadmium compound and replacing of a solvent Magnesium flakes (727 mg; 30 mmoles) were added to 20 ml of dried ether. The resulting suspension was heated at a bath temperature of 45° C., and with stirring, a solution of 2.81 ml (30 mmoles) of isopropyl bromide in 10 ml of dry ether was added dropwise. After the addition, the mixture was heated for 1 hour with stirring to dissolve the magnesium completely. The solution was cooled, and 4.36 g (16 mmoles) of a powder of anhydrous cadmium bromide was added. The mixture was heated at a bath temperature of 55° C. with stirring. Dry benzene (50 ml) was then added, and the ether was distilled off. With ice cooling (5° C.) and stirring, a solution in 10 ml of anhydrous benzene of 1.04 g (2.4 mmoles) of crude 3β-acetoxychol-5-enyl chloride obtained in the same way as in Example 1, (a) using 998 mg (2.4 mmoles) of 3β-acetoxychol-5-enic acid was added dropwise. After the addition, the mixture was stirred at room temperature for 1 hour, and 50 ml of cold water and 17 ml of 6 N hydrochloric acid were added dropwise to terminate the reaction.

After the reaction, suitable amounts of water and benzene were added to separate the reaction mixture into layers. The aqueous layer was extracted with benzene. The benzene extract was combined with the benzene layer. The mixture was washed with a saturated aqueous solution of sodium chloride, dried over anhydrous magnesium sulfate, filtered, and concentrated. The resulting solid crude product, 3β-acetoxy-24-oxocholest-5-ene, was purified by column chromatography, and then subjected to a hydrolysis reaction, and then isolated and purified. Thus, there was obtained 357 mg (yield 37% based on 3β-acetoxychol-5-enic acid) of 3β-hydroxy-24-oxocholest-5-ene as a white solid. The product had the same properties as shown in Example 1.

COMPARATIVE EXAMPLE 6

Conventional method involving the use as a solvent of dibutyl ether

Magnesium flakes (18.2 g; 0.75 mole) were added to 250 ml of anhydrous dibutyl ether. The resulting suspension was heated at a bath temperature of 45° C., and with stirring, a solution of 775 ml (0.825 mole) of isopropyl bromide in 125 ml of anhydrous dibutyl ether was added dropwise. After the addition, the mixture was heated with stirring for 2 hours to dissolve the magnesium completely. The solution was cooled, and 169 g (0.75 mole) of a powder of anhydrous zinc bromide was added. The mixture was heated at a bath temperature of 55° C. with stirring, and cooled. With ice cooling 5° C. and stirring, a solution of crude 3β-acetoxychol-5-enyl chloride obtained in the same way as in Example 1, (a) using 46.8 g (112.5 mmoles) of 3β-acetoxychol-5-enic acid in 375 ml of anhydrous benzene was added dropwise. After the addition, the mixture was stirred at room temperature for 1 hour, and further, 50 ml of cold water and 17 ml of 6 N hydrochlaoric acid were added dropwise to terminate the reaction.

After the reaction, suitable amounts of water and benzene were added to separate the reaction mixture into layers. The aqueous layer was extracted with benzene. The benzene extract was combined with the benzene layer. The mixture was washed with a saturated aqueous solution of sodium chloride, dried over anhydrous magnesium sulfate, filtered, and concentrated. The reslting solid crude product, 3β-acetoxy-24-oxocholest-5-ene, without purification, was subjected to a hydrolysis reaction in the same way as in Example 1, and then isolated and purified.

There was obtained 23.3 g (yield 52% based on 3β-acetoxychol-5-enic acid) of 3β-hydroxy-24-oxocholest-5-ene as a white solid. The product had the same properties as shown in Example 1.

What we claim is:

1. A process for producing a steriod compound having an oxo group in the side chain and expressed by the formula

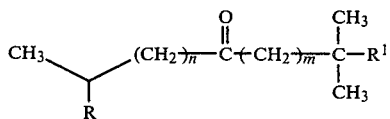

[I]

wherein R represents a steroid skeleton expressed by the following formula

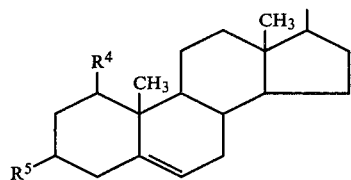

(a)

wherein $R^4$ represents a hydrogen atom or a protected hydroxyl group, $R^5$ represents a protected hydroxyl group,
or a steroid skeleton having a hydroxyl group or groups derived from a steroid skeleton of above formula (a) by means of hydrolysis, $R^1$ represents a hydrogen atom, a hydroxyl group or a hydroxyl group protected as an ether group, and n and m, independently from each other, represent O or an integer 1 to 4, provided that when m is O, $R^1$ is a hydrogen atom, which comprises condensing an acid halide of the formula

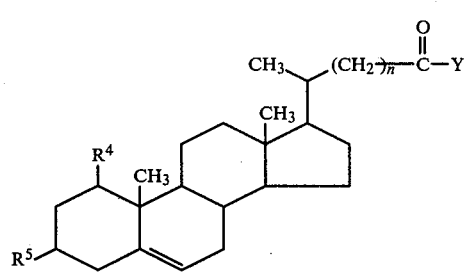

[III]

wherein $R^4$, $R^5$ and n are as defined above, and Y represents a halogen atom,
with an organozinc compound of the formula

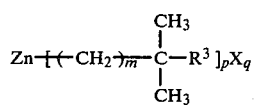

[II]

wherein $R^3$ represents a hydrogen atom or a hydroxyl group protected as an ether group, p is 1 or 2 and q is 0 or 1 provided that p+q=2, X represents a helogen atom, and m is as defined above,
in an inert organic medium in the presence of a catalytic amount of an ether capable of forming a complex with the organozinc compound, and optionally, hydrolyzing the resulting product.

2. The process of claim 1 wherein said ether contains one etheric oxygen atom in the molecule.

3. The process of claim 2 wherein said ether is an aliphatic or alicyclic ether.

4. The process of claim 3 wherein the aliphatic ether contains 2 to 10 carbon atoms.

5. The process of claim 3 wherein the alicyclic ether is a 5- or 6-membered cyclic ether.

6. The process of claim 1 wherein the amount of said ether is 0.1 to 2 moles per mole of the organozinc compound.

7. The process of claim 6 wherein the amount of said ether is 0.3 to 1.5 moles per mole of the organozinc compound.

8. The process of claim 1 wherein the condensation reaction is carried out in the substantial absence of water.

9. The process of claim 1 wherein the condensation reaction temperature is about $-20°$ C. to about 100° C.

10. The process of claim 1 wherein the organozinc compound is a compound of the formula

[II]-a wherein m, $R^3$ and X are defined with regard to formula [II].

11. The process of claim 1 wherein the organozinc compound is a compound of the formula

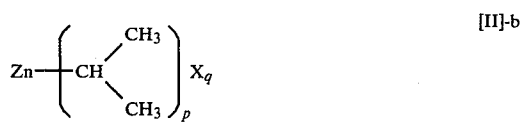

[II]-b wherein p, q and X are defined with regard to formula [II].

12. The process of claim 7 wherein the ether is selected from the group consisting of dimethyl ether, methyl ethyl ether, diethyl ether, diisopropyl ether, dibutyl ether, diamyl ether, tetrahydrofuran and tetrahydropyran.

13. A process for producing a steroid compound having an oxo group in the side chain and expressed by the formula

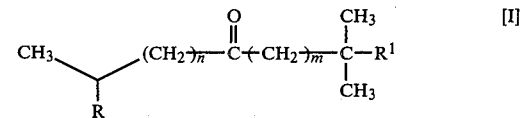

[I]

wherein R represents a steroid skeleton expressed by the following formula

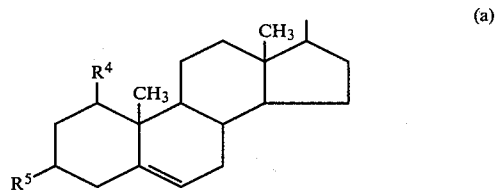

(a)

wherein $R^4$ represents a hydrogen atom or a protected hydroxyl group, $R^5$ represents a protected hydroxyl group, or a steroid skeleton having a hydroxyl group or groups derived from the steroid skeleton of above formula (a) by means of hydrolysis, $R^1$ represents a hydrogen atom, a hydroxyl group or a hydroxyl group protected as an ether group, and n and m, independently from each other, represent O or an integer 1 to 4, provided that when m is O, $R^1$ is a hydrogen atom, which comprises performing an addition reaction between metallic magnesium and an alkyl halide of the following formula

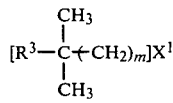   [IV]

wherein $R^3$ and m are as defined hereinabove and $X^1$ represents a halogen atom, in the presence of an ether in an inert organic medium to obtain a mixture containing an organomagnesium compound of the formula

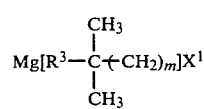   [V]

wherein $R^3$, $X^1$ and m are as defined above, adding a zinc halide of the formula $Zn(X^2)_2$   [IV]

wherein $X^2$ represents a halogen atom, to the resulting mixture to obtain a mixture containing an organozinc compound of the formula

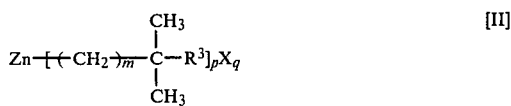   [II]

wherein $R^3$, m, p and q are as defined hereinabove, and X represents a halogen atom represented by $X^1$ or $X^2$, and a catalytic amount of the ether capable of forming a complex with the organozinc compound, adding an acid halide of the formula

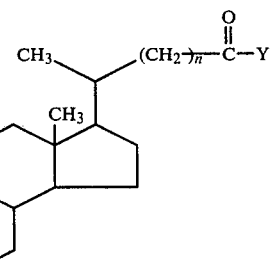

wherein $R^4$, $R^4$ and n are as defined above, and Y represents a halogen atom, to perform the condensation reaction between the organozinc compound and the acid halide, and optionally hydrolyzing the resulting product.

* * * * *